United States Patent
Yousefian

(10) Patent No.: US 10,478,270 B2
(45) Date of Patent: Nov. 19, 2019

(54) DENTAL ARCH AND AIRWAY EXPANDER DEVICE AND METHOD

(71) Applicant: Joseph Yousefian, Bellevue, WA (US)

(72) Inventor: Joseph Yousefian, Bellevue, WA (US)

( * ) Notice: Subject to any disclaimer, the term of this patent is extended or adjusted under 35 U.S.C. 154(b) by 0 days.

(21) Appl. No.: 15/599,736

(22) Filed: May 19, 2017

(65) Prior Publication Data

US 2017/0252127 A1 Sep. 7, 2017

Related U.S. Application Data

(63) Continuation-in-part of application No. 14/931,566, filed on Nov. 3, 2015, now Pat. No. 10,004,574.

(60) Provisional application No. 62/502,086, filed on May 5, 2017, provisional application No. 62/074,360, filed on Nov. 3, 2014.

(51) Int. Cl.
| | |
|---|---|
| A61C 7/10 | (2006.01) |
| A61C 7/18 | (2006.01) |
| A61C 7/16 | (2006.01) |
| A61C 7/28 | (2006.01) |

(52) U.S. Cl.
CPC .................. *A61C 7/10* (2013.01); *A61C 7/18* (2013.01); *A61C 7/282* (2013.01); *A61C 7/16* (2013.01)

(58) Field of Classification Search
CPC .... A61C 7/10; A61C 7/18; A61C 3/00; A61C 7/282; A61C 7/16
USPC .......................... 433/17, 19, 18, 7, 20, 21, 22
See application file for complete search history.

(56) References Cited

U.S. PATENT DOCUMENTS

| | | | |
|---|---|---|---|
| 1,938,426 A | 12/1933 | Johnson | |
| 3,477,129 A | 11/1969 | Rubin | |
| 3,832,778 A * | 9/1974 | Wallshein | A61C 7/10 433/7 |
| 4,571,178 A * | 2/1986 | Rosenberg | A61C 7/10 433/18 |
| 5,399,087 A | 3/1995 | Arndt | |
| 5,769,631 A * | 6/1998 | Williams | A61C 7/10 433/7 |
| 5,816,800 A | 10/1998 | Brehm et al. | |
| 5,829,970 A * | 11/1998 | Yousefian | A61C 7/00 433/21 |
| 6,033,216 A | 3/2000 | Souris | |
| 6,220,856 B1 * | 4/2001 | Carano | A61C 7/10 433/7 |
| 6,402,510 B1 | 6/2002 | Williams | |
| 6,520,772 B2 | 2/2003 | Williams | |

(Continued)

*Primary Examiner* — Heidi M Eide
*Assistant Examiner* — Mirayda A Aponte
(74) *Attorney, Agent, or Firm* — Timothy E. Siegel Patent Law, PLLC; Timothy E. Siegel

(57) ABSTRACT

An oral appliance that attaches to molars or bicuspids and that combines the capability for side-to-side and front-to-back expansion and contraction in one unit as a self-stopping mechanism. Further, this embodiment can be activated to compress or expand and be deactivated in two planes of side-to-side or front-to-back, along three different arms/bridges respectively. This is to say that one arm can compress front-to-back while the other arm expands, the jaw/teeth front-to-back, simultaneously). With proper arrangements and anchorage preparation the device shown and described can move front teeth forward or backward or back teeth forward or backward independently on either side of the mouth.

6 Claims, 15 Drawing Sheets

(56) References Cited

U.S. PATENT DOCUMENTS 7,500,851 B2     3/2009   Williams

* cited by examiner

DENTAL ARCH AND AIRWAY EXPANDER DEVICE AND METHOD

RELATED APPLICATIONS

This application is a continuation-in-part of application Ser. No. 14/931,566 filed on Nov. 3, 2015, which in turns claims benefit of provisional application Ser. No. 62/074,360 filed Nov. 3, 2014, and also claims benefit of co-pending provisional application Ser. No. 62/502,086 filed on May 5, 2017, all of which are incorporated by reference as if fully set forth herein.

BACKGROUND

Orthodontists, dental practitioners and medical-dental researchers are constantly searching for new and improved ways to correct the problem of constriction of the dental arches that also contribute to the overcrowding or overlapping of teeth. This condition, by narrowing of the tongue space and retraction of the tongue back to the airway, can cause the constriction of the upper airway in the retropalatal (behind the palate), retroglossal (behind the tongue) and hypoglossal (behind and below the tongue) area. As a result, the upper airway of the patient becomes constricted and causes resistance to the air passage, especially during the deeper stage of sleep when the upper airway muscles relax and cannot provide ideal support for the patency of the airway.

In the past, many different methods have been used in order to alleviate the constriction and collapse of dental arches and dental crowding. One method that has been utilized by orthodontic practitioners is that of dental expansion of the upper and lower dental arch as well as dental and or orthopedic expansion of the upper jaw in transverse direction. There have also been attempts to do so by front-to-back expansion of the dental arches by advancing the upper or lower anterior teeth forward or distalizing (retracting) the upper and lower back teeth further backward. Although the combination of these two protocols means expansion in transverse and front to back plane of space and makes more logical process, there have not been any appliance designs capable of combining these two protocols.

One dental arch expander device on the market today is a lower lingual arch to advance mandibular incisors. It does not require activation or de-activation chair side adjustments. This appliance is capable of front-to-back expansion only. As a result, it cannot expand the side to side or transverse relationship of dental arch. Another drawback of this system is that it needs to be customized for each patient (e.g., in a laboratory) and cannot be provided in a kit for a chairside use.

Another dental arch expander device that is on the market today is depicted in FIG. 1 and sometimes is referred to as the Arnold expander device. The Arnold expander device 100 develops the arch using a spring-loaded split-lingual arch housed in a tube. More specifically, the Arnold expander device 100 includes a wire 102, a spring coil 104, a tube 106, and bands 108. The spring coil 104 passes into the tube 106 to create the spring-loaded split-lingual arch. The bands 108 anchor the device 100 to the patient's molar teeth. Tension on the spring coil 104 is set before the device 100 is initially placed. Further adjustment is not usually necessary. Once the desired space has been created, the appliance can be made passive by carefully pinching the tube 106 tight against the wire 102 with a pair of heavy wire cutters or tube crimping pliers. This device 100 is not capable of advancing the dental arches from back to front or distalizing the back teeth.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Embodiments of dental arch and airway expander devices described herein provide improved orthodontic appliances for use in nasal cavity and/or dental arch expansion for the purpose of correcting dental crowding and/or providing tongue space for treating the upper airway constriction caused by retraction of the tongue and constriction of the nasal cavity. In some embodiments, the appliance includes left and right molar attachment portions, each of which, in some embodiments, is securable to the patient's left or right first or second molars on the right and left side of the mouth in the upper or lower jaw. In some embodiments, there are sliding wires that connect to the tongue side of the molar bands using removable tubes. In some embodiments, each tube has two inserts that slide vertically to slots soldered or otherwise attached to the tongue side of the attachment portions. In some embodiments, sliding wires that connect to the tongue side of the attachment portions using non-removable connection tubes are soldered or otherwise attached to the lingual side of the attachment portions. A sheath can be provided in a front area behind the upper and lower front teeth of the appliance to connect the right and left extensions of the wires. This sheath provides a sliding slot as a telescopic system such that the anterior ends of the wires, bent as hooks in some embodiments, can slide freely toward or away from each other for purpose of expansion or constriction. In some embodiments, there are two loaded springs (e.g., compression springs) sliding freely over the right and left side wire compressed between the connector tubes attached to the attachment portions and the sheath in front. These loaded springs can be used to produce an outward force between the connector tubes coupled to the left and right attachment portions in the back and front connector tube behind the anterior teeth. The term "anterior teeth" refers essentially to the canines and incisors.

In some embodiments, sliding wires connect to the tongue side of the attachment portions using removable connector tubes. In some embodiments, each tube has two inserts that slide vertically to slots soldered or otherwise attached to the tongue side of the attachment portions. This connector tube provides a sliding slot as a telescopic system such that the posterior end of the sliding wires on each side of the mouth, bent as hooks in some embodiments, can slide freely backward or forward for purpose of sagittal (front-to-back) expansion or constriction of the dental arch. In some embodiments, there are two loaded springs sliding freely over the right and left side wires compressed between the posterior connector tubes attached to the attachment portions and the sheath in front. These springs can be used to produce an expansion or constriction spring force in a sagittal direction between the anterior sheath and posterior connection tubes connected to the left and right attachment portions.

In one example, the connector tubes are coupled to the attachment portions via an attachment system for easy attachment and removal of the connector tubes to and from the attachment portions. In one example, the attachment system has self-locking capability. Also, as a safety feature, the connector tubes and attachment portions can be locked with wire to prevent unintended disengagement of the connector tubes from the attachment portions. In one example, the attachment portions include bonding that bonds the connector tubes to the lingual side of the patient's molars. In one example, a portion of the connector tubes is flat with no inserts for proper fit of the connector tubes to the lingual surfaces of first or second upper or lower molars. In this design, the flat end of tubes can be bonded to the lingual surface of first or second molars with no need for the attachment portions to include a band around the molars. This option makes the appliance esthetically enhanced with no features extending on the labial surface of the molars. In some embodiments, the connector tubes are soldered or otherwise fixedly attached to the tongue side of molar bands of the attachment portions.

In one example, the connector tubes are coupled to the attachment portions using an attachment system for easy attachment and removal of the connector tubes to and from the attachment portions. In one example, the attachment system has self-locking capability. Also, as a safety feature, the connector tubes and attachment portions can be locked with wire to prevent unintended disengagement of the connector tubes from the attachment portions. One benefit to this appliance is that it requires less maintenance and has fewer parts, therefore being less cumbersome and more cosmetically appealing for the patient. Another benefit is that the appliance is less expensive because it requires less hardware and maintenance.

Embodiments of dental arch and airway expander appliances described herein create lateral expansion of the nasal cavity as well as lateral expansion or constriction of the posterior teeth (second and first molars, second and first bicuspids) while advancing the position of the anterior teeth (canines and incisors) and distalizing (or moving back) the posterior teeth. Once the posterior teeth are expanded to their desired position, either the expander device stops further expansion automatically as determined by the set size of expansion width or can be inactivated. Adjustments of the expander device can be made without removal from the patient's mouth. The insertion assembly to the molar tubes is removable for adjustment without damage or discomfort to the patient.

Further, the position of the device behind the teeth on the roof of the mouth or floor of the mouth along with the singular connection to the molar bands creates a device that is less obtrusive to the patient and therefore more cosmetically desirable. A singular connection point on the lingual side of the molar band also allows for connection of various devices, such as braces or headgear, to the buccal side of the band.

In another example, the sheath placed lingual to incisor teeth along with sliding wires can be curved to conform to the lingual side of the incisors. This alteration can be done at the chairside in the beginning or during the treatment progress. This option provides more ideal positioning of the incisors and canines during or at the completion of the advancement of the anterior teeth.

In some embodiments, these attachment portions include bonding or cementation on the occlusal and/or labial surface of upper or lower first or second bicuspids, can be used in conjunction with class two or class three type mechanical devices or rubber bands to be utilized to advance or retract that dental arch in relationship to the opposite dental arch in sagittal direction for proper improvement of class two or class three malocclusions to class one relationship. This option, combined with use of fixed type three or type two mechanical devices, reduces the patient's noncompliance failure.

In embodiments, springs form a part of the device and are used to apply a user determined amount of pushing or pulling force to the teeth being treated. FIGS. 8 and 9 show an embodiment that combines side-to-side and front-to-back expansion capability in one unit as a self-stopping mechanism. Further, this embodiment can be activated to compress or expand and be deactivated in two planes of side-to-side or front-to-back, along three different arms/bridges respectively. This is to say that one arm can compress front-to-back while the other arm expands, the jaw/teeth front-to-back, simultaneously. With proper arrangements and anchorage preparation the device shown and described can move front teeth forward or backward or back teeth forward or backward independently on either side of the mouth.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The process of dental arch development is designed to move the back teeth posteriorly as well as laterally and front teeth anteriorly in the mouth to allow room for the other teeth and to expand the circumference of the dental arches larger to correct the dental crowding and to accommodate space for the volume of tongue allowing the forward positioning of the tongue out of the pharyngeal air space. When designing a product to perform this lateral and backward and frontal positioning of the teeth, two factors may be considered. The first factor is how to make a product that performs this type of tooth movement in an efficient manner. The second factor is how to make a product that is functional for the user, comfortable for patient, as well as cosmetically appealing without inhibiting the tooth movement process.

For effectiveness and convenience of practitioner and patient, a dental arch and airway expander orthodontic appliance should limit periodic activation or deactivation by chair side adjustments, but at the same time have self-limiting capability to avoid unwanted expansion and/or advancement of the teeth. The self-limiting capability avoids unwanted movements in case the patient misses an appointment to be checked by the practitioner. When patient compliance is an issue, a fixed appliance is always preferred.

Once the desired lateral expansion has been created, the appliance should either stop by its self-limiting capability, be made passive by carefully pinching the sheath tight on both sides against the wire with a pair of heavy wire cutters or tube crimping pliers, or tying the sliding wires inside of the tube using a stainless ligature wire.

Once the desired sagittal expansion and space has been created, the appliance should either stop on its own, be made passive by carefully bending the sliding wire behind the tube attached to the first and second molars, or tying the bent end of the sliding wires inside of the connector tubes using stainless ligature wire to a hook which is welded to the inside of the molar bands.

Figure 2A:
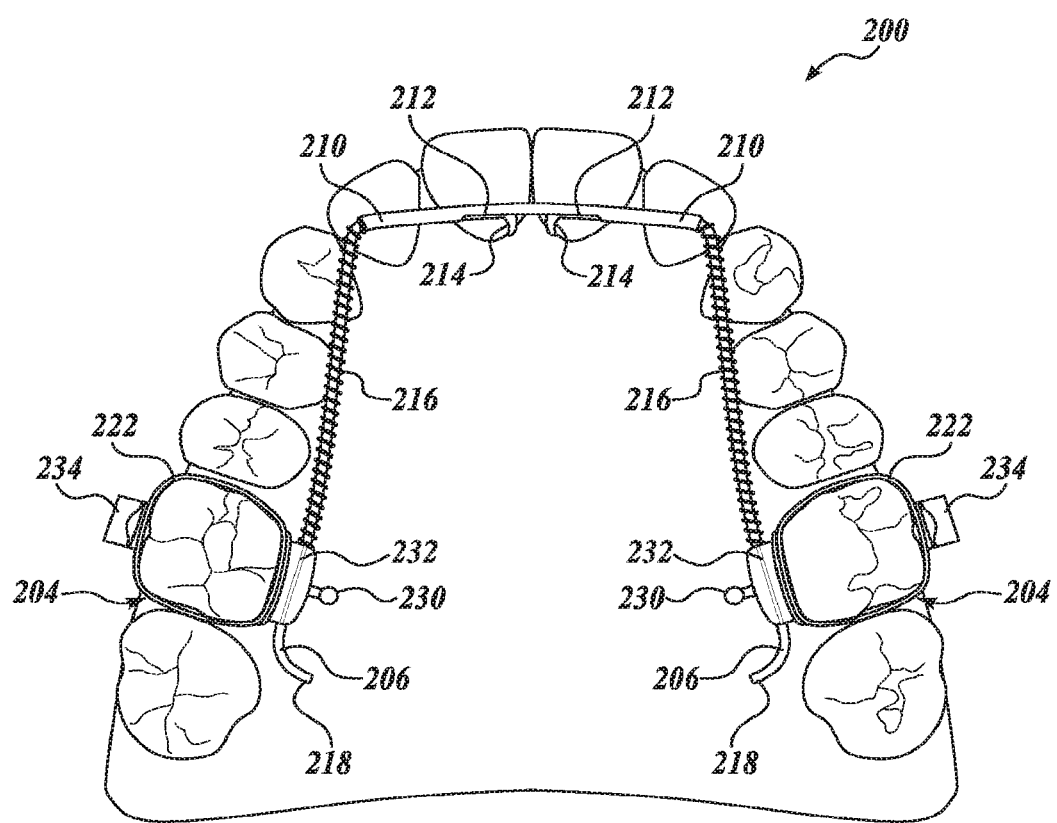
FIG. 2A depicts a view of an embodiment of a dental arch and airway expander orthodontic appliance, in accordance with the embodiments disclosed herein, being worn on the upper jaw and teeth of a patient.

FIG. 2A illustrates an embodiment of a dental arch and airway expander orthodontic appliance 200. FIG. 2A depicts the upper palate of a patient with the appliance 200 resting on the lingual side of the upper teeth. The appliance 200 includes an arch portion 202 (FIG. 2B) on the lingual side of the upper teeth and attachment portions 204 attached to the patient's first molars. In the embodiment shown in FIG. 2A, the appliance 200 has a U shape that is fitted to the patient's upper or lower teeth. In some embodiments, including the embodiment shown in FIG. 2A, the appliance 200 includes left and right halves that are symmetrical.

Figure 2B:
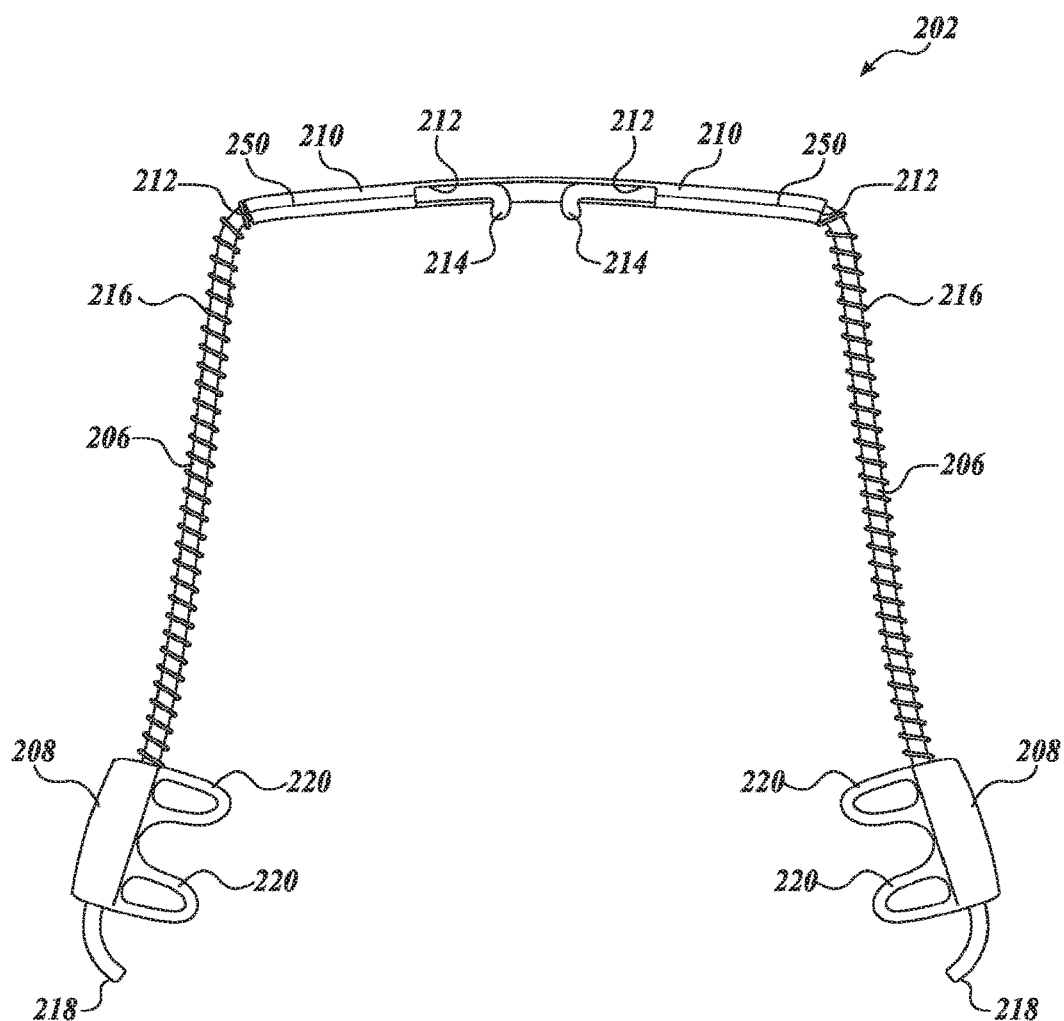
FIG. 2B depicts a bottom view of the arch portion of the dental arch and airway expander orthodontic appliance depicted in FIG. 2A.

The arch portion 202, which is depicted in greater detail in FIG. 2B, includes two sliding wires 206 that pass inside of connector tubes 208. In some embodiments, the sliding wires 206 are stainless steel wires. The connector tubes 208 are configured to be coupled to the attachment portions 204. In some embodiments, each of the connector tubes 208 includes one or more inserts 220 configured to couple the connector tubes 208 to the attachment portions 204. Each of the wires 206 extends into a sheath 210 which is positioned inside of the anterior teeth. In some embodiments, the sheaths 210 are stainless steel sheaths. Each of the sheaths 210 has an opening 212. In some embodiments, the openings 212 are positioned to face the palate or floor of the mouth of the patient. Each of the wires 206 has an anterior end 214 in the front of the mouth that is bent into the opening 212. The wires 206 are capable of sliding freely inside of the sheaths 210 until the anterior ends 214 contact the sides of the openings 212. In the depicted embodiment, the sheaths 210 include seams 250. In practical implementation, the sheaths 210 may originally be in an open configuration with the seams 250 open such that the wires 206 may be inserted into the sheaths 210. Then, after the wires 206 are inserted into the sheaths 210, the seams 250 can be closed to the configuration shown in FIG. 2B so that the wires 206 are kept in place.

Loaded springs 216 are located around the wires 206 between the connector tubes 208 and the sheaths 210. The sheaths 210 are used for holding and connecting the anterior ends 214 of the wires 206 when the force generated by the expansion springs 216 expands. The sheaths 210 connect the two halves of the appliance 200 and maintain relative spacing between the wires 206. In some embodiments, the sheaths 210 are integrally formed as a single piece. The lengths of openings 212 in the sheaths 210 determine the maximum expansion width of the appliance 200. The anterior ends 214 of the wires 206 slide inside the sheaths 210 by force generated by the loaded springs 216 until the bent anterior ends 214 touch the right or left side of the openings 212. In this way, the openings 212 in the sheaths 210 function as stops to limit the maximum lateral expansion of the appliance 200.

In some embodiments, when in place and fully activated, the wires 206 laterally extend within the sheaths 210 inside of the upper or lower anterior teeth directly behind the incisors with a 2- to 3-mm space left between the sheaths 210 and the bicuspid teeth. In some embodiments, the anterior ends 214 of the wires 206 are prefabricated with a bent formation in the last 1.5 mm. In some embodiments, the anterior ends 214 are positioned inside of the openings 212 of sheaths 210, the wires 206 extend laterally to almost touching the first bicuspids, and then the wires 206 are bent distally and toward the back of mouth. The wires 206 extend and pass through the inside of the connector tubes 208. In some embodiments, the wires 206 extend between 6 mm and 10 mm toward the back of the mouth.

Figure 1:
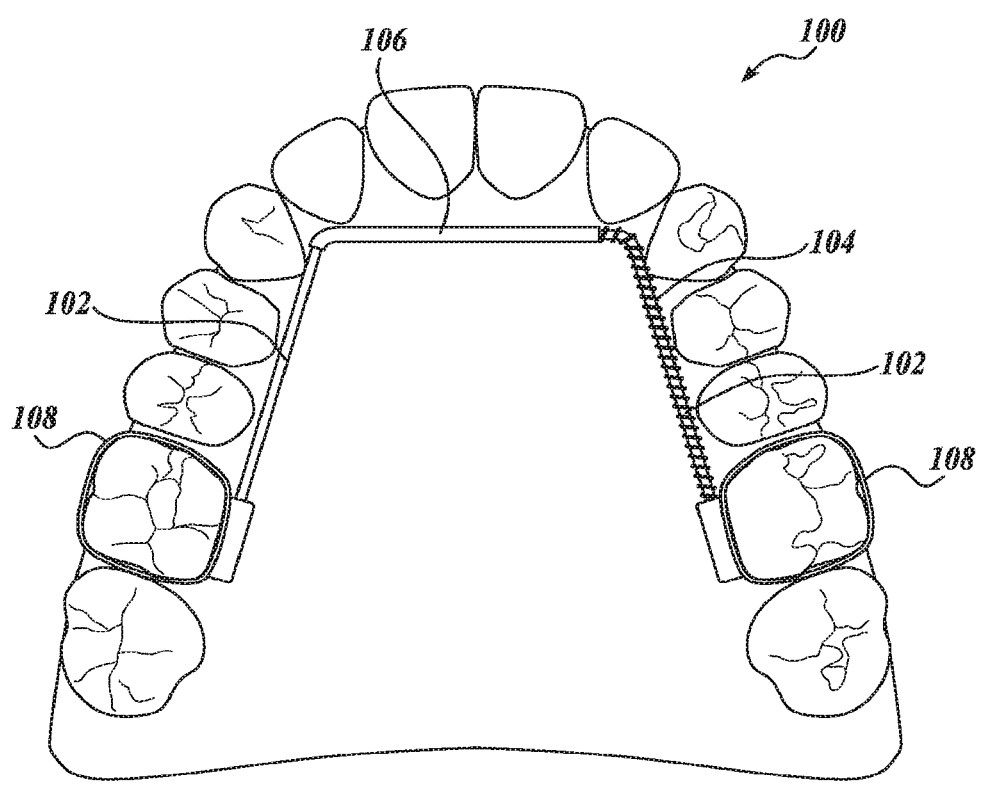
FIG. 1 depicts a prior art dental arch expander device.

In the embodiment shown, the wires 206 have posterior ends 218 that are bent toward the roof or floor of the patient's mouth. In some embodiments, the bend at the posterior ends 218 of the wires 206 is about 90 degrees. In some embodiments, the bend at the posterior ends 218 is either prefabricated or made by the clinician at the time of installation of the device in the patient's mouth. The bent posterior ends 218 function as self-limiting stops. In the depicted embodiment, the force of the expander springs 216 causes the wires 206 to slide in the connector tubes 208 until the bent posterior ends 218 of the wires 206 touch the distal ends of the connecting tubes 208. In some embodiments, the location of the bends on the posterior ends 218 of the wires 206 is selected such that the bends on the posterior ends 218 of the wires 206 will reach the connector tubes 208 when the desired advancement of the anterior teeth is reached. If during the treatment, a clinician determines that enough advancement of the anterior teeth has been acquired, the clinician can create a bend in one or both of the wires 206 extending distal of the connector tubes 208 at the chairside without removal of the device. Creating such a bend can prevent further advancement of the anterior teeth. This is a significant advantage over other devices, such as the device 100 (FIG. 1) which does not have self-limiting capability, allowing overextension of the wire 102 to disengage the wire 102 from the tube 106 and leave the spring coil 104 loose.

Figure 2C:
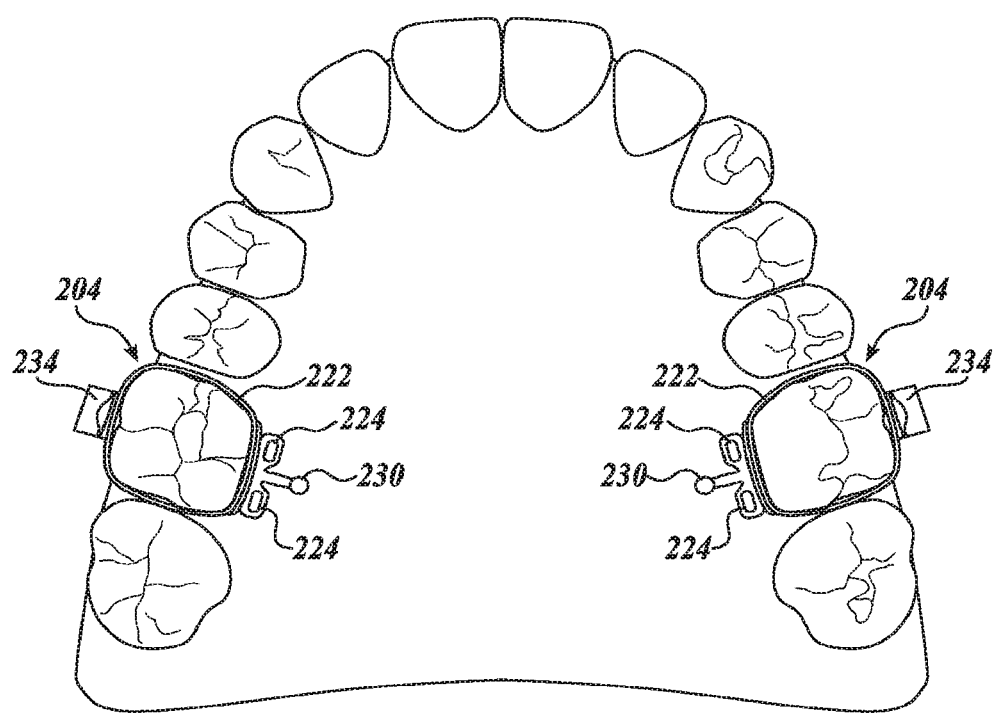
FIG. 2C depicts a view of upper jaw and teeth of a patient with first molar bands of the dental arch and airway expander orthodontic appliance depicted in FIG. 2A.
Figure 2D:
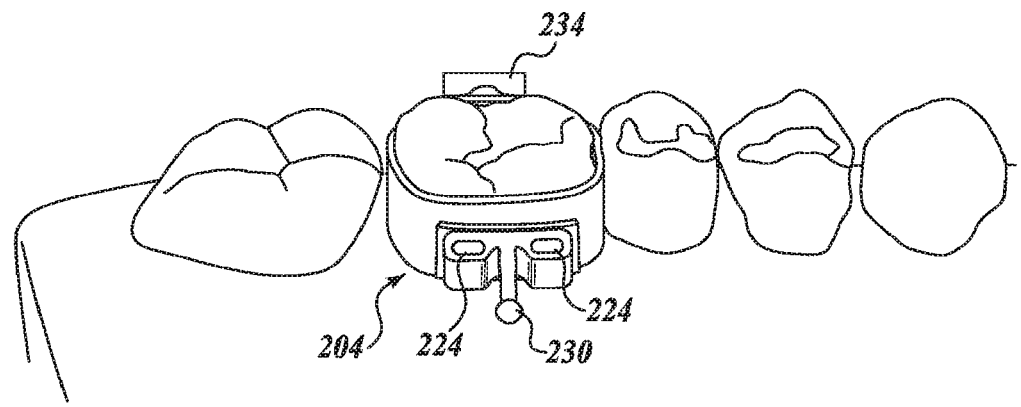
FIG. 2D depicts a view of a molar tooth of a patient with first molar band of the dental arch and airway expander orthodontic appliance depicted in FIG. 2A.

During installation of the appliance 200, the connector tubes 208 are coupled to the attachment portions 204. The attachment portions 204 are depicted in greater detail in FIGS. 2C and 2D. Each of the attachment portions 204 include a band 222 configured to be anchored on one of the patient's teeth (e.g., on a molar). The attachment portions 204 include slots 224 located on an inward portion of the bands 222. In one embodiment, the slots 224 are oriented in a vertical from occlusal to gingival direction on the lingual side of the first molars in maxillary and mandibular arches. Each slot 224 is open at least on the occlusal and/or gingival end to accommodate insertion of the inserts 220 into the slots 224. In some embodiments, the slots 224 are located approximately at the middle of the lingual part of the bands 222 horizontally and the openings are directed vertically, with the opening of the slots 224 at the middle of vertical height of the bands 222 on the lingual side of the first molar. In some embodiments, the location of the slots 224 is prefabricated and welded to the band 222 in the factory or can be welded in the lab later. In other embodiments, the connector tube 208 is welded to the band 222 in the lab to form a coupling between the arch portion 202 and the attachment portions 204 without the use of the inserts 220 and the slots 224.

Figure 2E:
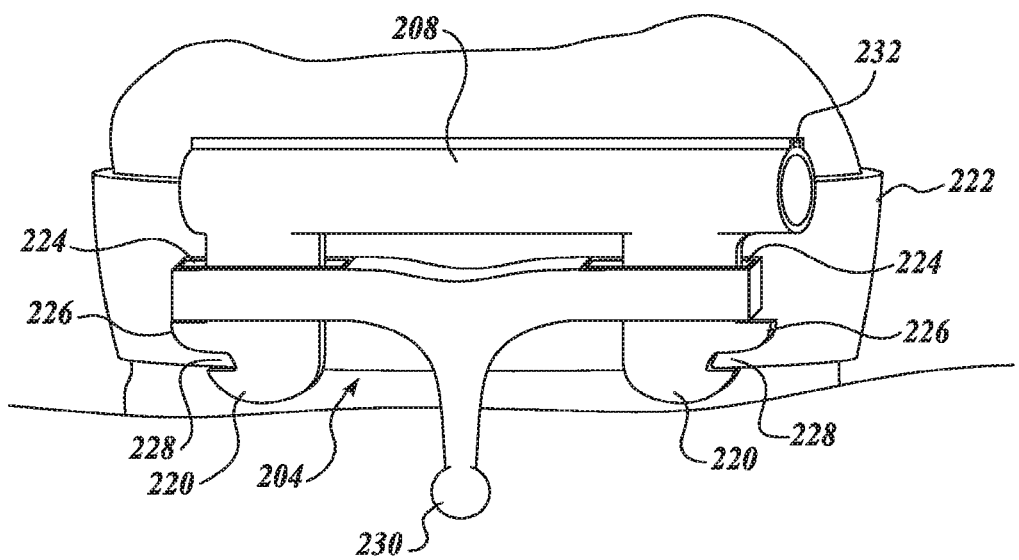
FIG. 2E depicts another view of a molar tooth of a patient with first molar band, in accordance with the embodiments disclosed herein.

In some embodiments, the inserts 220 of the connector tubes 208 are removably insertable into and securely coupled to the slots 224 on the patient's first or second molars. An embodiment of a connector tube 208 coupled to an attachment portion 204 is depicted in FIG. 2E. In the embodiment shown, each of the inserts 220 has a locking mechanism 226 that, after passing through the slots 224, extend beyond the opening of the slots 224 by spring activation to prevent unintended dislodging of the inserts 220 from the slots 224. In some embodiments, the inserts 220 also include an unlocking mechanism 228 configured to permit the inserts 220 to be removed from the slots 224. In the embodiment shown in FIG. 2E, the unlocking mechanisms 228 are in the form of slots below the locking mechanisms 226. A tool (e.g., a wire director device) can be inserted into the unlocking mechanisms 228 and used to push the inserts 220 towards each other. This motion pushes the locking mechanisms 226 into the slots 224 such that the inserts 220 can be removed from the slots 224 for removal of the connector tube 208 from the attachment portion 204.

In the embodiments depicted in FIGS. 2A and 2C to 2E, each of the attachment portions 204 includes a hook 230 coupled to the lingual side of the band 222. Each connector tube 208 has, on the occlusal side, a notch 232. The hook 230 and the notch 232 are usable for further prevention against any unintended disengagement of the connector tube 208 from the attachment portions 204. More specifically, a practitioner may wind a wire around the hook 230 and the notch 232 to prevent relative motion of the connector tube 208 and the band 222. In some embodiments, the bands 222 also have a connecting piece 234 attached to its buccal side. The connecting pieces 234 are attachable to various conventional orthodontic devices, such as wires in braces or connection assemblies from other class II mechanisms, class III mechanisms, or any other class of mechanisms.

In some embodiments of constructing the arch portion 202, the wire 206 is inserted into the sheath 210, through the loaded spring 216, and then into the connector tube 208. To install the arch portion 202 on the attachment portions 204, the inserts 220 of the connector tubes 208 are inserted into the slots 224 of the attachment portions 204. In some embodiments, the wire 206 has a diameter in a range from about 0.030 inches to about 0.060 inches. In some embodiments, the wire 206 extends posteriorly towards the molars approximately parallel to the lingual side of the molars. The posterior end of wire 206 passes through the connector tubes 208 attached to the molar band and, in some embodiments, extends about 6 mm to 10 mm beyond the distal portion of the connector tubes 208. At the posterior ends 218 of the wire 206, the wire 206 bends vertically about 1 mm. In some embodiments, the posterior ends 218 are slightly slanted laterally to avoid irritating the patient's tongue. In some embodiments, the inserts 220 of the connector tubes 208, which are inserted in the slots 224 welded on the inside of the bands 222, are secured by tying a wire ligature around the notch 232 on the occlusal portion of the connector tubes 208 and around the hook 230 and/or to extension of the inserts 220 that extend beyond the slots 224. When wire 206 is in place, the expansion spring 216 maintains contact at one end with the open end of the sheath 210 and on the other end to the connector tube 208.

Figure 3:
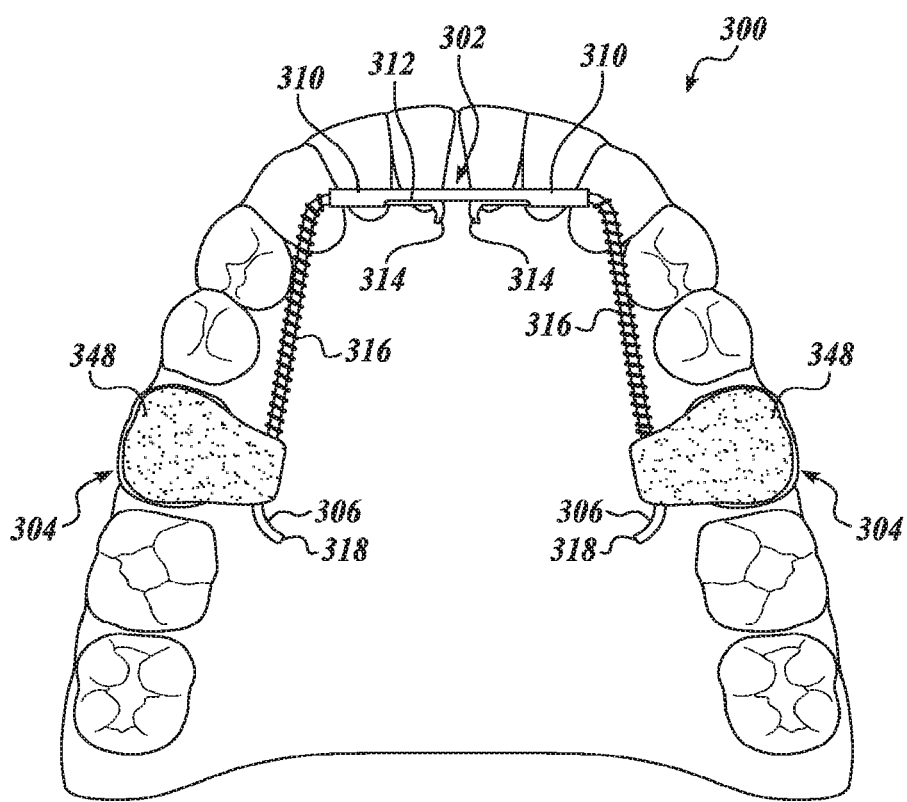
FIG. 3 depicts a view of another embodiment of a dental arch and airway expander orthodontic appliance, in accordance with embodiments disclosed herein, being worn on the lower jaw and teeth of a patient.

An alternate embodiment of a dental arch and airway expander orthodontic appliance 300 is depicted in FIG. 3. The appliance 300 includes an arch portion 302 on the lingual side of patient's teeth and attachment portions 304 attached to the patient's molars. The arch portion 302 includes wires 306 that pass inside of connector tubes (Not Shown). The connector tubes are configured to be coupled to the attachment portions 304. The wires 306 extend into a sheath 310 which is positioned inside of the anterior teeth. The wires pass inside the sheaths 310. The sheaths 310 have openings 312 through which anterior ends 314 of the wires 306 are permitted to extend. The wires 306 are capable of sliding freely inside of the connector tubes and inside of the sheath 310. Loaded springs 316 are located around the wire 306 between the connector tubes and the sheath 310. In some embodiments, the attachment portions 304 and the connector tubes are similar to the attachment portions 204 and the connector tubes 208 described above.

In the depicted embodiment, the attachment portions 304 include bonding medium 348 configured to attach the connector tubes 308 to the occlusal surface of molar, or bicuspids. In some embodiments, the connector tubes include one or more bonding mechanisms, such as a single mesh layer, a double mesh layer, a bonding pad, a hinged boding pad, or any other mechanism to aid in the attachment of the bonding medium 348 to the connector tubes 308. Such bonding mechanisms are described in greater detail below with respect to FIGS. 5A and 5B.

In the embodiment shown in FIG. 3, the appliance 300 is configured to expand laterally as the wires slide within the sheaths 310 in response to the force exerted by the loaded springs 316. In other embodiments, the appliance 300 is configured to expand sagittally as the wire 306 slides within the connector tubes in response to the force exerted by the loaded springs 316. In contrast to the expander device 100 depicted in FIG. 1, the lateral and sagittal expansion of the appliance 300 can be relatively symmetrical with substantially similar forces exerted by each of the loaded springs 316. The lateral and sagittal expansion of the appliance 300 can also be intentionally asymmetrical with substantially dissimilar forces exerted by each of the loaded springs 316.

In some embodiments, the wires 306 are formed as two wires 306 where the anterior ends 314 of the two wires 306 are bent and located in openings 312 of the sheath 310 and the posterior ends 318 of the two wires 306 are bent after the two wires 306 are fed through the connector tubes.

Figure 4A:
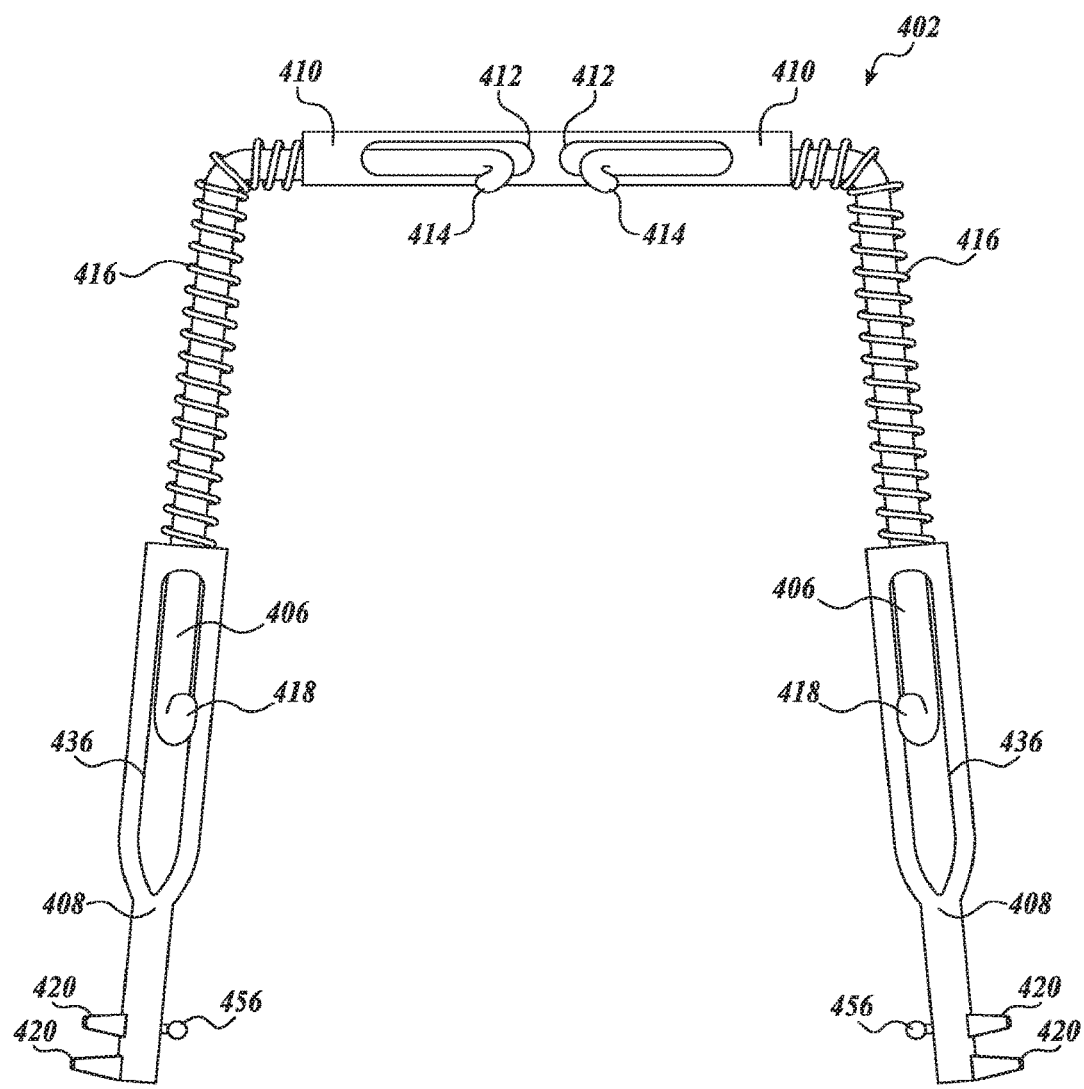
FIG. 4A depicts a view of another embodiment of a dental arch and airway expander orthodontic appliance.
Figure 4B:
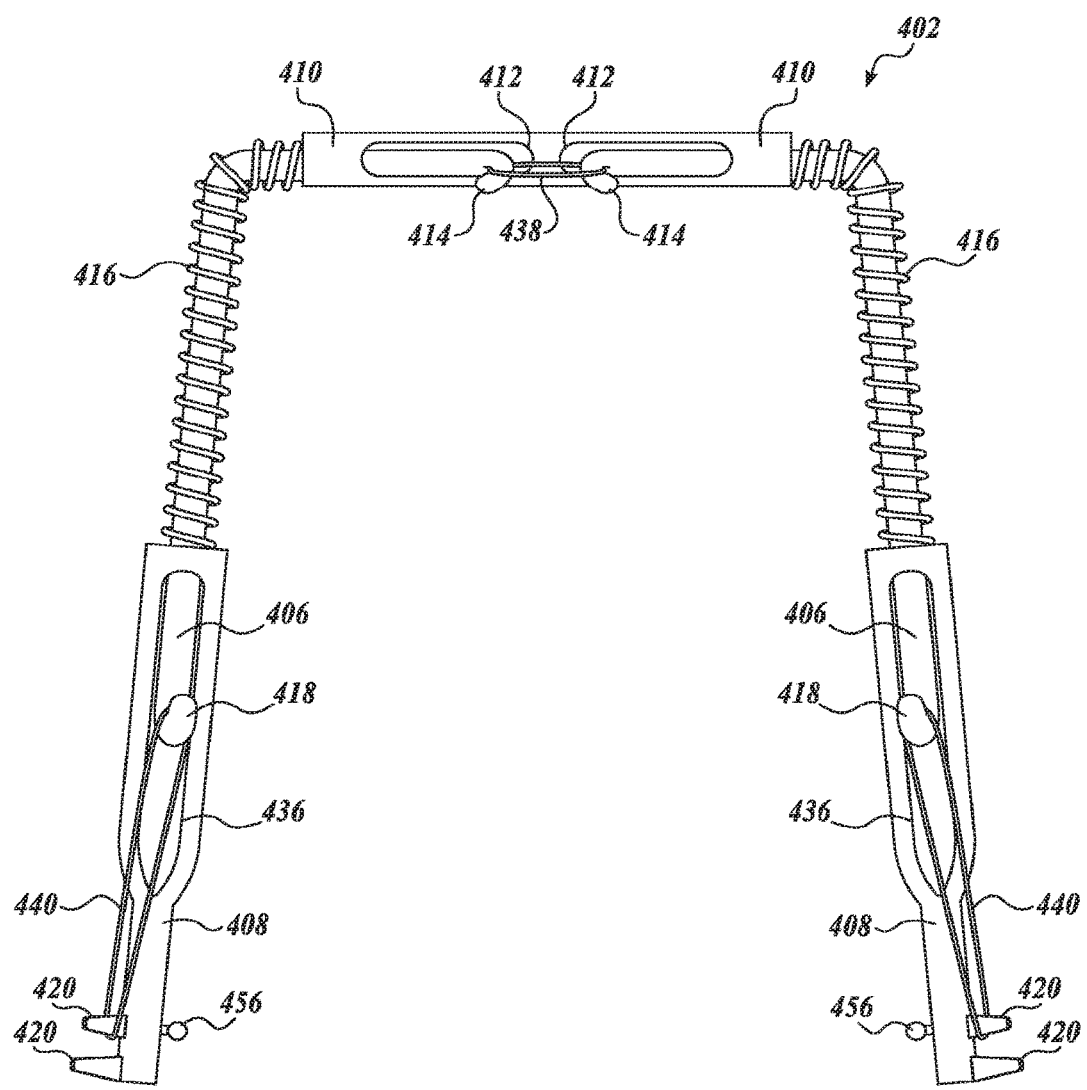
FIG. 4B depicts a view of the bottom of another embodiment of the appliance depicted in FIG. 4A.

An alternate embodiment of an arch portion 402 of a dental arch and airway expander orthodontic appliance is depicted in FIGS. 4A and 4B. The arch portion 402 includes connector tubes 408 that are closed at the posterior end. Posterior ends 418 of wires 402 pass through anterior openings of the connector tubes 408. The posterior ends 418 are bent through openings 436 in the connector tubes 408. In some embodiments, the posterior ends 418 are bent vertically about 1 mm and slightly slanted laterally to avoid irritating the patient's tongue. In some embodiments, the posterior ends 418 of the wires 406 are capable of sliding about 6 mm to 10 mm inside the openings 436 of the connector tubes 408.

Each of the wires 406 extends into a sheath 410 which is positioned inside of the anterior teeth. Each of the sheaths 410 has an opening 412. In some embodiments, the openings 412 are positioned to face the palate or floor of the mouth of the patient. Each of the wires 406 has an anterior end 414 in the front of the mouth that is bent into the opening 412. The wires 406 are capable of sliding freely inside of the sheaths 410 until the anterior ends 414 contact the sides of the openings 412. Loaded springs 416 are located around the wires 406 between the connector tubes 408 and the sheaths 410. The force generated by the loaded springs 416 causes the patient's arch to expand laterally as the anterior ends 414 of the wires 406 slide within the openings 412 of the sheath 410. The force generated by the loaded springs 416 also causes the patient's arch to expand sagittally as the posterior ends 418 of the wires 406 slide within the openings 436 of the connector tubes 408.

In some embodiments, the connector tubes 408, which are closed at their posterior end, are coupled to attachment portions (e.g., attachment portions 204 depicted in FIG. 2A). The posterior ends 418 of the wires 406 are bent (e.g., in the last 1.5 mm) and positioned inside of the openings 436 of connector tubes 408. The wires 406 extend anteriorly to almost touching the first bicuspids then bend inwardly and extend and pass through inside the sheath 410. In case the full advancement capability of appliance is desired, then this process continues until the bent posterior ends 418 of the wires 406 are touching the front sides of the openings 436 inside connector tube 408, preventing further withdrawal of the wire 406 from the connector tube 408, and thereby limiting spread of the patient's anterior teeth to this predetermined extent. The posterior ends 418 act as self-limiting stops by touching the anterior portion of the openings 436 in connecting tubes 408 when the desired advancement of the anterior teeth is reached.

In FIG. 4A, the bent anterior ends 414 of the wires 406 and the bent posterior ends 418 of the wires 406 are free to slide within the sheaths 410 and the connector tubes 408. If, during treatment, a clinician determines that enough advancement of the anterior teeth has been acquired, the clinician may tie the bent anterior ends 414 of the wires 406 together and/or the bent posterior ends 418 of the wires 406 to inserts 420 or to any other portion of the arch portion 402, such as posterior notches (e.g., to posterior notches 544 discussed below) to prevent further expansion of the arch portion 410 laterally and/or sagitally. In FIG. 4B, a first wire 438 is tied between the bent anterior ends 414 of the wires 406. The first wire 438 prevents lateral expansion of the arch portion 402 because the first wire 438 does not permit the wires 406 to move away from each other. In case where lateral constriction of the dental arch is desired, the first wire 438 shown in FIG. 4B can be replaced by constricting elastic or spring between the bent anterior ends 414 of the wires 406. The elastic or spring is configured to constrict the arch portion 402 because the elastic or spring pulls the wires 406 toward each other if the constriction of the dental arch is desired to close existing spaces. In this case, where lateral constriction of the dental arch is desired, the springs 416 may be removed, cut, or otherwise inactivated such that the springs 416 do not exert an expanding lateral force on the arch portion 402.

Second wires 440 are tied between the bent posterior ends 418 of the wires 406 and inserts 420 on the connector tubes 408. The second wires 440 prevent sagittal expansion of the arch portion 402 because the second wires 440 do not permit the wires 406 to move away from the connector tubes 408. In other embodiments, the clinician can tie the bent posterior ends 418 of the wires 406 to hooks 456 extending from the connector tubes 408. In one embodiment, the posterior end 418 of each wire 406 that is received within the connector tube 408 is bent in the shape of a hook. By tying these bent posterior ends 418 using a stainless steel second wire to the hook of the attachment portion, the advancement or distalization expansion of the appliance can be stopped short of final expansion limit. In an alternative embodiment, the posterior ends 418 of the wires 406 which extend beyond the connector tubes 408 may be removed, which may make it easier for some patients to tolerate the appliance.

In the case where sagittal constriction of the dental arch is desired, the second wires 440 may be replaced by constricting elastic or springs, which are tied between the bent posterior ends 418 of the wires 406 and inserts 420 on the connector tubes 408. The elastic or spring is configured to pull the wires 406 toward the connector tubes 408 to constrict the arch portion 402 in a sagittal direction. In other embodiments, the clinician can tie the bent posterior ends 418 of the wires 406 to hooks 456 extending from the connector tubes 408 using elastic or springs that may allow for sagittal constriction of the arch portion 402. In one embodiment, the posterior end 418 of each wire 406 that is received within the connector tube 408 is bent in the shape of a hook. By tying these bent posterior ends 418 using constricting elastics or springs to the hook of the attachment portion, the front teeth can be retracted back and/or the posterior teeth can be protracted forward. In this case, the springs 416 may be removed, cut, or otherwise inactivated such that the springs 416 do not exert an expanding sagittal force on the arch portion 402.

Figure 5A:
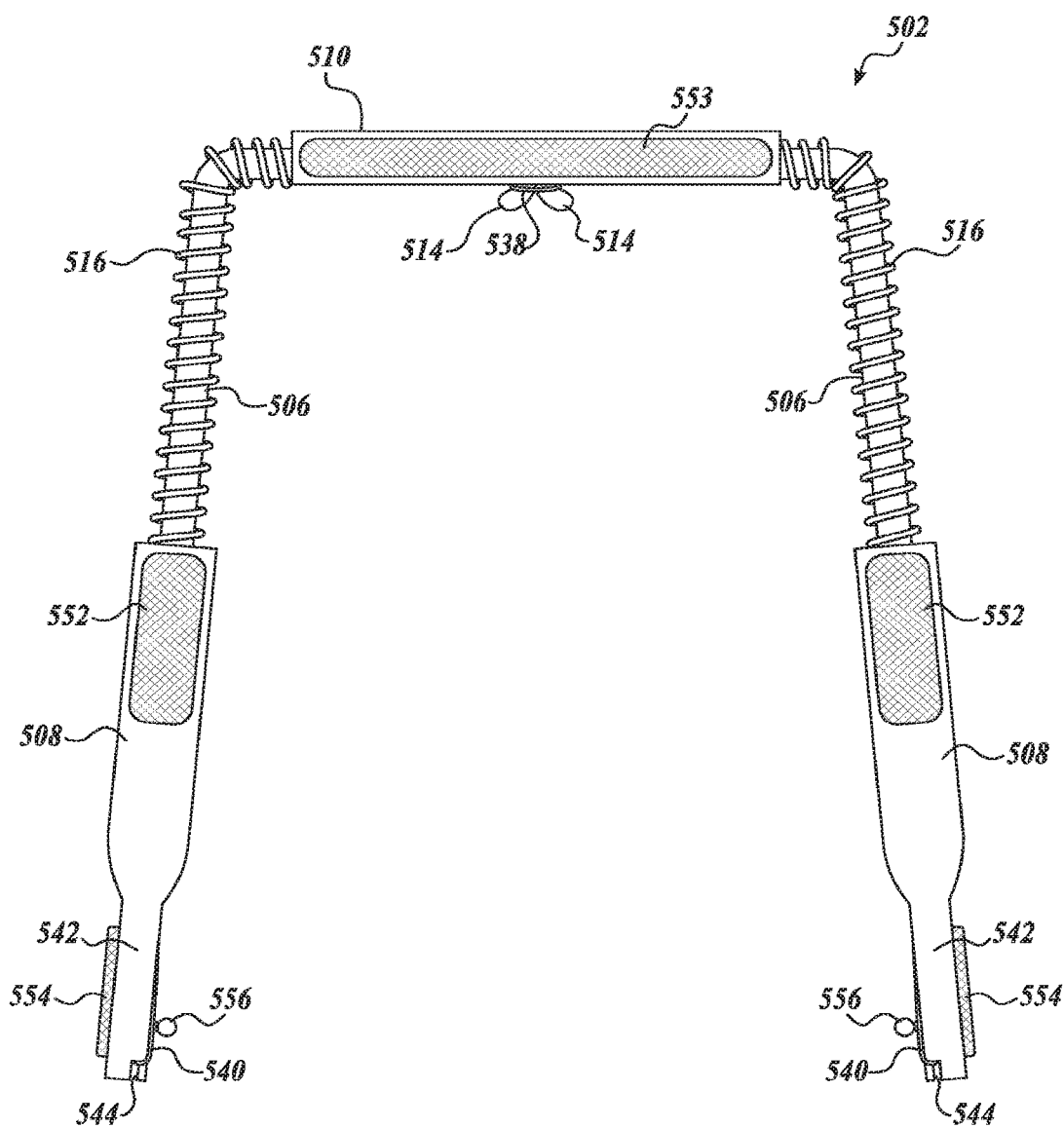
FIG. 5A depicts a view of a top of another embodiment of a dental arch and airway expander orthodontic appliance.
Figure 5B:
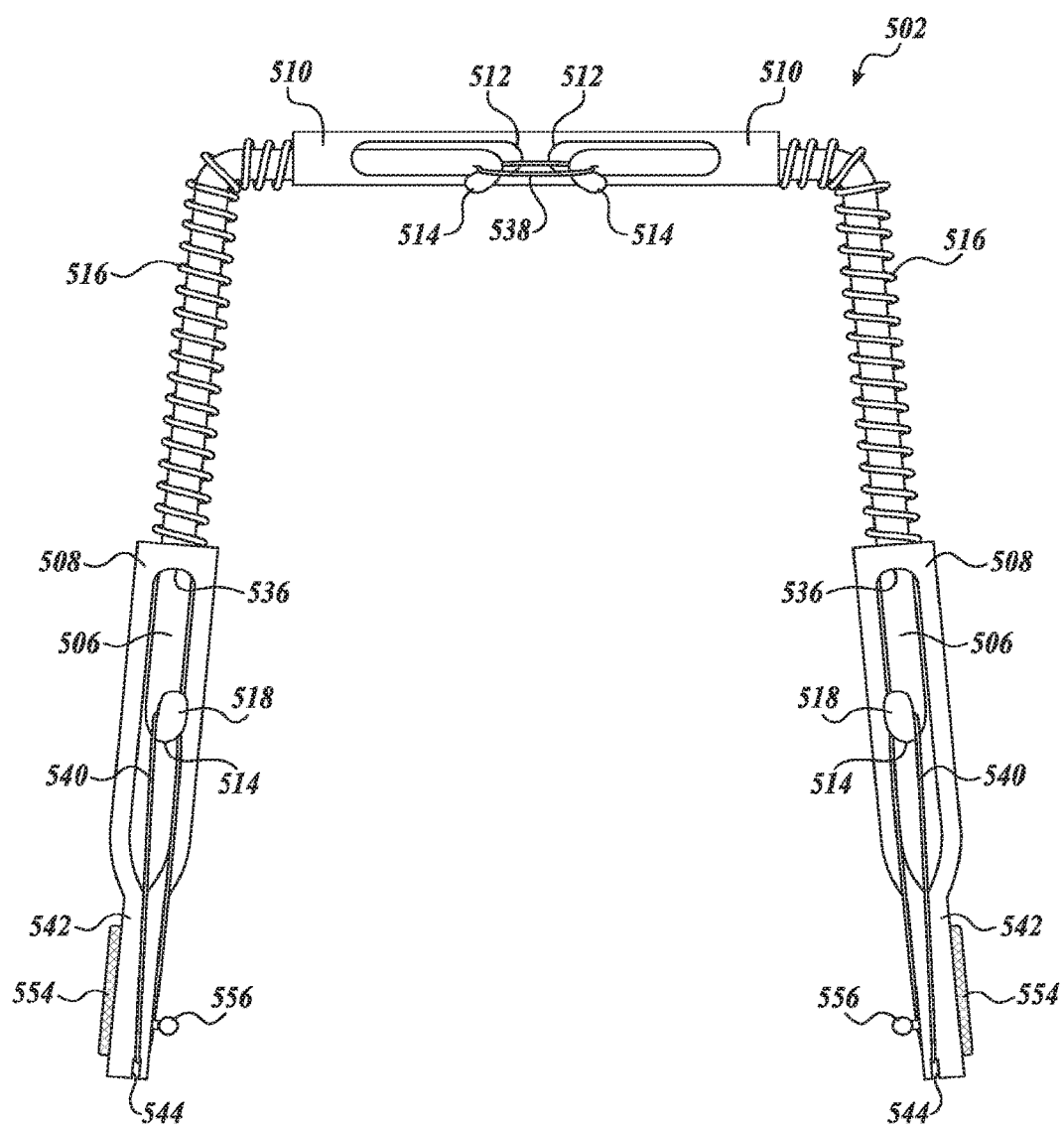
FIG. 5B depicts a bottom view of the embodiment of the appliance depicted in FIG. 5A.
Figure 5C:
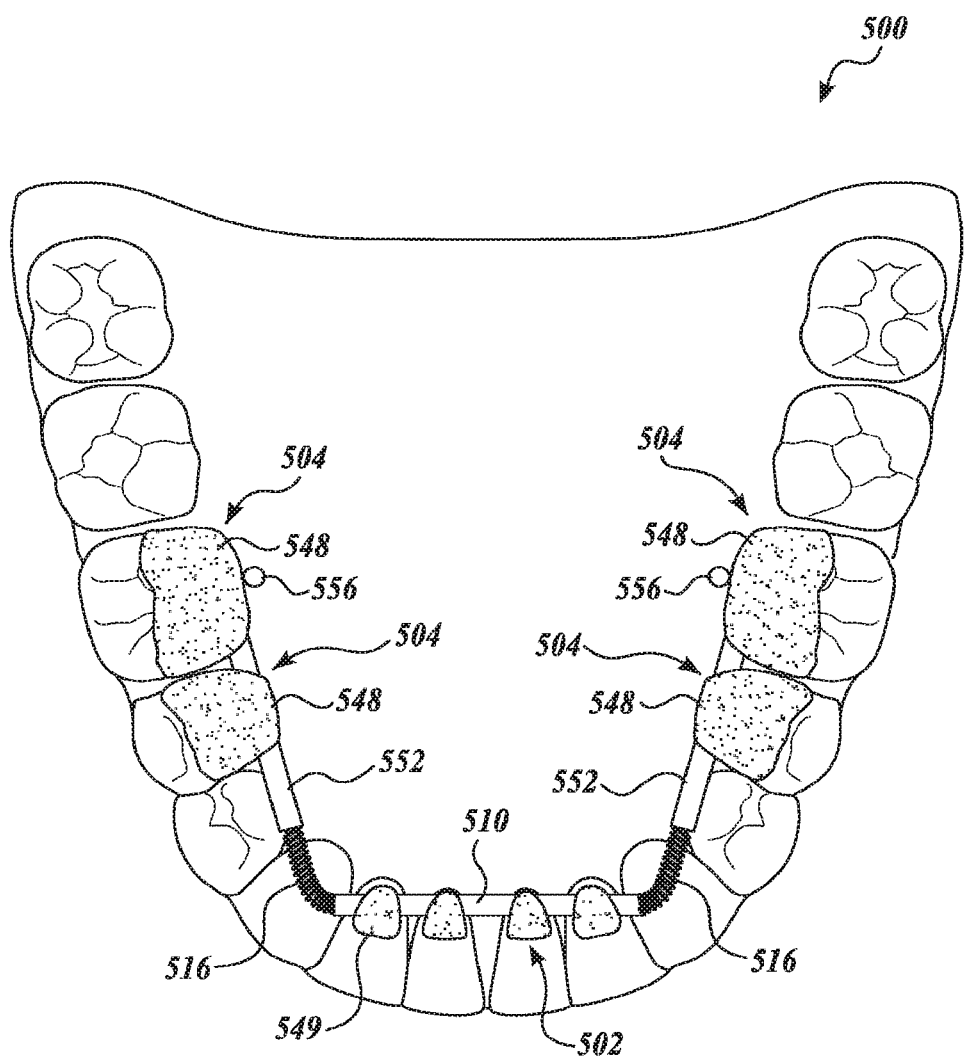
FIG. 5C depicts the appliance depicted in FIG. 5A with attachment portions as bonding to lower teeth of a patient.

An alternate embodiment of an arch portion 502 of a dental arch and airway expander orthodontic appliance 500 is depicted in FIGS. 5A and 5B. The appliance 500 placed in a patient's mouth is depicted in FIG. 5C. The arch portion 502 includes connector tubes 508 that are closed at the posterior end. Posterior ends 518 of wires 506 pass through anterior openings of the connector tubes 508. The posterior ends 518 are bent through openings 536 in the connector tubes 508. Each of the wires 506 extend into a sheath 510 which is positionable inside of the anterior teeth. Each of the sheaths 510 has an opening 512. In some embodiments, the openings 512 are positioned to face the palate or floor of the mouth of the patient. Each of the wires 506 has an anterior end 514 in the front of the mouth that is bent into the opening 512. The wires 506 are capable of sliding freely inside of the sheaths 510 until the anterior ends 514 contact the sides of the openings 512. Loaded springs 516 are located around the wires 506 between the connector tubes 508 and the sheaths 510.

In the embodiments shown in FIGS. 5A and 5B, lateral expansion of the arch portion 502 is prevented by a first wire 538 and sagittal expansion of the arch portion 502 is prevented by second wires 540. The first wire 538 is tied between the bent anterior ends 514 of the wires 506. The first wire 538 prevents lateral expansion of the arch portion 502 because the first wire 538 does not permit the wires 506 to move away from each other. Second wires 540 are tied between the bent posterior ends 518 of the wires 506 and posterior notches 544 on the connector tubes 508. The second wires 540 prevent sagittal expansion of the arch portion 502 because the second wires 540 do not permit the wires 506 to move away from the connector tubes 508. In some embodiments, the arch portion 502 includes hooks 556 and the second wires 540 could be tied between the bent posterior ends 518 of the wires 506 and hooks 556 instead of the posterior notches 544. In some cases, the posterior notches 544 will be covered with a bonding medium when placed in a patient's mouth and the hooks 556 may extend out from the bonding medium. In these cases, the hooks 556 may be usable after bonding even if the posterior notches 544 are not usable. In some embodiments, the arch portion 502 includes the hooks 556 but not the posterior notches 544 (e.g., in the case that the posterior notches 544 irritate the patient's mount).

In some embodiments, the first wire 538 and the second wires 540 are placed on the arch portion 502 before the arch portion 502 is inserted into a patient's mouth to prevent premature expansion of the arch portion 502. The first wire 538 and the second wires 540 are then removed after the arch portion 502 is inserted into a patient's mouth to permit expansion of the arch portion 502 within the patient's mouth. Each of the connector tubes 508 includes a flat portion 542. The connector tubes do not include inserts (e.g., inserts 220). Instead of tying the bent posterior ends 518 of the wires 506 to inserts, a clinician can tie the posterior ends 518 of the wire 506 to the posterior notches 544 at the most posterior end of the flat portions 542 of connector tubes 508 by the second wires 540.

In the case where lateral and/or sagittal constriction of the arch portion 502 is desired, the first wire 538 and/or the second wire 540 can be replaced by an elastic or a spring configured to exert a constricting force on the bent anterior ends 514 of the wires 506 or the bent posterior ends 518 of the wires 506, respectively. The replacement of the first wire 538 and/or the second wire 540 with an elastic and/or a spring is similar to the replacement of the first wire 438 and/or the second wire 440 with an elastic and/or a spring, as discussed above.

In some embodiments, the occlusal portion of sheath 510 and/or the anterior ends of the connector tubes 508 and/or the flat portions 542 are configured to be bonded to the lingual surface of a patient's molars and/or anterior teeth. In the depicted embodiment, the anterior ends of the connector tubes 508 include bonding mechanisms 552, the occlusal portion of sheath 510 includes a bonding mechanism 553, and the flat portions 542 of the connector tubes 508 include bonding mechanisms 554. In one example, one or more of the bonding mechanisms 552-554 is a single mesh plate, such as a seventy-micron mesh design that is welded or soldered as a prefabricated design to enhance the bonding strength of bonding medium to the connector tubes 508 and/or anterior sheath 510. In another example, a one or more of the bonding mechanisms 552-554 is a double mesh plate with two single mesh plates overlaid on each other. In another example, one or more of the bonding mechanisms 552-554 includes a surface treatment, such as a sand-blasted surface, that is configured to improve adherence of the bonding medium when bonding to the connector tubes 508 and/or anterior sheath 510. In another example, one or more of the bonding mechanisms 552-554 includes a bonding pad configured to improve adherence of the bonding medium when bonding to the connector tubes 508 and/or anterior sheath 510. In some embodiments, the bonding pad is usable in combination with other bonding mechanisms (e.g., a bonding pad with a single or double mesh layer). In another example, the one or more of the bonding mechanisms 552-554 includes a hinged bonding pad which is hingedly fixed to the anterior ends of the connector tubes 508, the sheath 510, and/or the flat portions 542. In some examples, the hinged bonding pad includes a hinge with a vertical axis, a hinge with a horizontal axis, or a ball hinge that rotates in multiple directions. The hinged pad is configured to rotate in one or more directions and/or extended laterally to better engage the patient's tooth. Examples of ball hinged pads are described below with respect to FIGS. 6A and 6B.

Depicted in FIG. 5C, is the appliance 500 with the arch portion 502 and the attachment portions 504. In this embodiment, the attachment portions 504 include bonding medium 548 configured to attach the connector tubes 508 (e.g., to bonding mechanism 552 on the flat portion 542) to the occlusal surface of molar, or bicuspids. The bonding medium 548 prevents the displacement of the arch portion 502 toward the occlusal. In another embodiment, bonding medium 549 is configured to attach to a portion of the sheath 510 (e.g., bonding mechanism 553) to the lingual surface of anterior teeth including incisors and canines. The bonding medium 549 prevents displacement of the arch portion 502 toward the occlusal or facilitates the bodily movement instead of tipping of the anterior teeth in saggital expansion or constriction of the dental arch. While the bonding medium 548 is shown only with respect to the appliance 500, any of the other appliances described herein may include an attachment portion that includes a bonding material or any other coupling mechanism instead of the insert-and-slot coupling mechanisms described above. As shown in this embodiment, the hooks 556 protrude from the bonding medium 548 and can be used to tie the bent posterior ends 518 (FIG. 5B) of the wires 506.

Figure 6A:
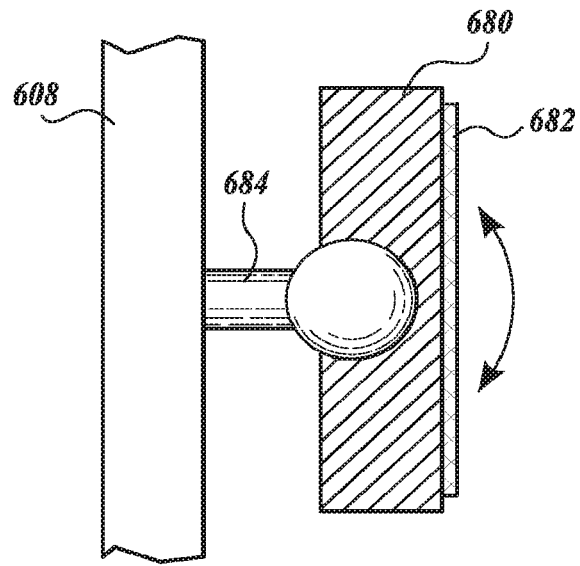
FIG. 6A depicts an embodiments of ball hinged pads, usable in accordance with any of the bonding mechanisms described herein.
Figure 6B:
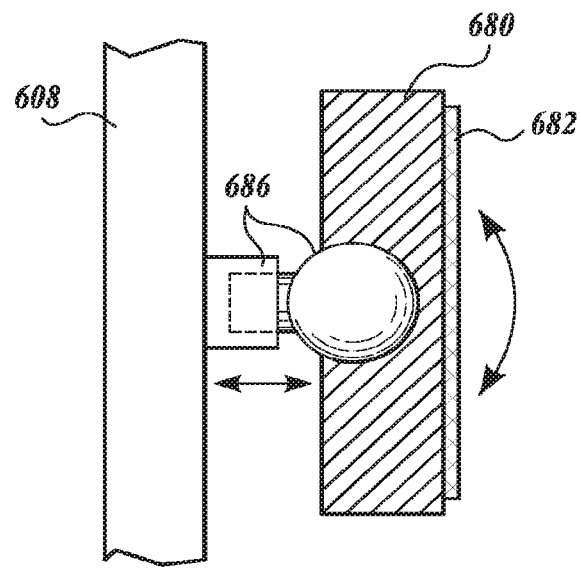
FIG. 6B depicts an additional embodiment of ball hinged pads, usable in accordance with any of the bonding mechanisms describes herein.

Depicted in FIGS. 6A and 6B are embodiments of ball hinged pads, usable in accordance with any of the bonding mechanisms described herein. FIG. 6A depicts an embodiment of a bonding pad 680 with a bonding surface 682. In some embodiments, the bonding surface 682 includes a single mesh layer, a dual mesh layer, a surface treatment, or any other bonding surface. The pad 680 is coupled to a connector tube 608 via a fixed-length ball hinge arm 684. The fixed-length ball hinge arm 684 extends a fixed distance away from the connector tube 608 and permits the pad 680 to rotate in one or more directions to better engage the patient's tooth. FIG. 6B depicts an embodiment of the bonding pad 680 with the bonding surface 682. The pad 680 is coupled to a connector tube 608 via a telescopic ball hinge arm 686. The telescopic ball hinge arm 686 extends away from the connector tube 608 a variable length, which can be adjusted by the practitioner to an appropriate distance to engage the patient's tooth. The telescopic ball hinge arm 686 permits the pad 680 to rotate in one or more directions to better engage the patient's tooth.

Figure 7A:
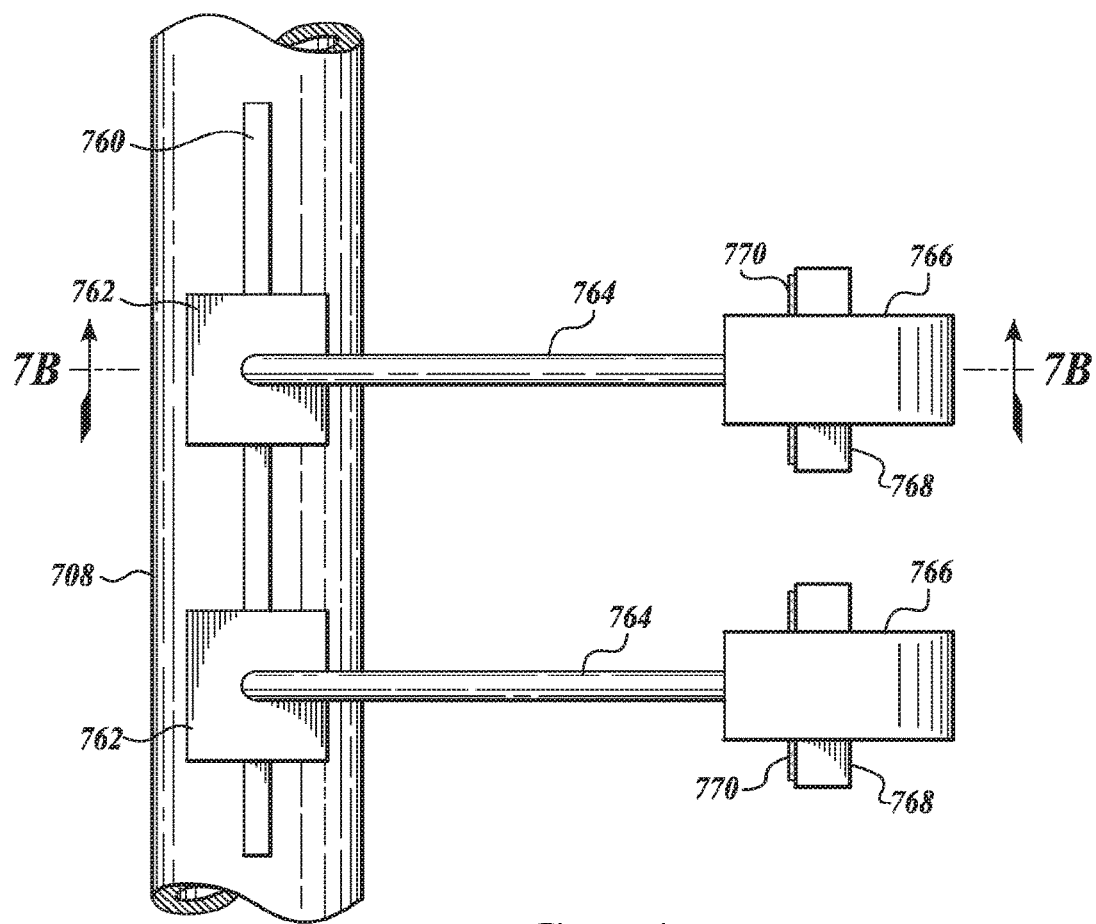
FIG. 7A depicts a top view, of a connecting system for connecting various conventional orthodontic devices when the attachment portion does not include a band around the molar or bicuspids.
Figure 7B:
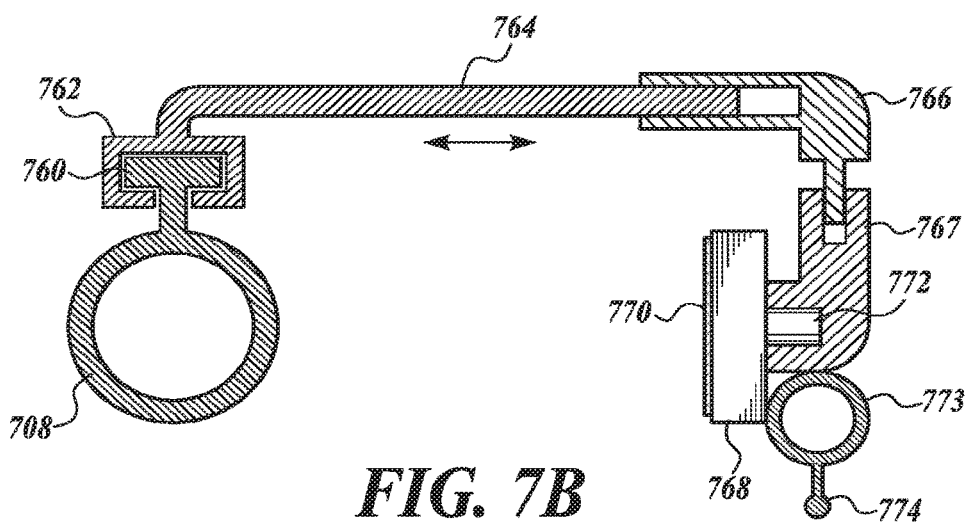
FIG. 7B depicts a cross-sectional view of a connecting system for connecting various conventional orthodontic devices when the attachment portion does not include a band around the molar or bicuspids.

FIGS. 7A and 7B depict top and cross-sectional views, respectively, of a connecting system for connecting various conventional orthodontic devices when the attachment portion does not include a band around the molar. The connecting system includes a track 760 fixedly attached to the top of a connector tube 708. A crimpable clasp 762 is located around the track 760. In some embodiments, the crimpable clasp 762 is slidable along the track 760 to be properly positioned. When properly located along the track, the crimpable clasp 762 can be crimped onto the track 760 by a practitioner to prevent further sliding of the crimpable clasp 762 along the track 760. In some embodiments, the crimpable clasp 762 has a cross-sectional shape corresponding to the cross-sectional shape of the track 760. For example, in the depicted embodiment, the track 760 has a cross-sectional "T" shape and the crimpable clasp 762 has a cross-sectional rectangular shape with an opening for the stem of the T-shaped track 760.

An extension arm 764 extends from the crimpable clasp 762 and engages an upper extension attachment 766. The upper extension attachment 766 engages a lower extension arm 767. The lower extension arm is coupled to a bonding pad 768 with a bonding mechanism 770 (e.g., a single layer mesh, a double layer mesh, etc.) on a surface of the pad 768 facing the connector tube 708. The upper extension attachment 766 is configured to move telescopically with respect to the extension arm 764 such that the distance between bonding mechanism 770 and the connector tube 708 is variable. The connector tube 708 is configured to be placed on the lingual side of the tooth and the bonding mechanism 770 is configured to contact the facial side of the tooth, with the occlusal side of the tooth facing the extension arm 764. When the upper extension attachment 766 is in the desired position (e.g., with the connector tube 708 on the lingual side of a tooth and the bonding mechanism in contact with the facial side of the tooth), a practitioner can crimp the upper extension attachment 766 on the extension arm 764 to prevent relative movement of the crimpable clasp 762 with respect to the upper extension attachment 766. The lower extension attachment 767 is configured to move telescopically with respect to the upper extension attachment 766 such that the vertical location of bonding mechanism 770 is variable (e.g., the location of the bonding mechanism 770 can be moved to contact the bottom, middle, or top portion of the tooth). When the lower extension attachment 767 is in the desired position, a practitioner can crimp the lower extension attachment 767 on the upper extension attachment 766 to prevent relative movement of the upper extension attachment 766 with respect to the lower extension attachment 767.

The upper extension attachment 766 can slide along the extension arm 764 telescopically to a desired distance between the crimpable clasp 762 and the upper extension attachment 766. When the upper extension arm 766 is in the desired position, a practitioner can crimp the upper extension attachment 766 on the extension arm 764 to prevent relative movement of the crimpable clasp 762 with respect to the upper extension attachment 766. The upper extension attachment 766 engages a lower extension attachment 767. The lower extension attachment 767 can slide along the upper extension attachment 766 telescopically to a desired distance between the upper extension attachment 766 and the lower extension attachment 767. When the lower extension arm 767 is in the desired position, a practitioner can crimp the lower extension attachment 767 on the upper extension attachment 766 to prevent relative movement of the upper extension attachment 766 with respect to the lower extension attachment 767.

In some embodiments, the lower extension attachment 767 forms a slot 772 or other attachment mechanism. In some embodiments, a tube 773 or other attachment mechanism is coupled to the lower extension attachment 767 and the pad 768. In some examples, the tube 773 has a width equal to or less than the upper and lower extension attachments 766 and 767. In some embodiments, the tube 773 includes a hook 774 extending therefrom. In some examples, the hook 774 extends substantially vertically down from the tube 773. The hook 774 is usable to secure ends of wires of arch portions described herein, to secure orthodontic appliances to the connector tube 708, or to secure any other appliance in the patient's mouth.

In some embodiments, the slot 772, the tube 773, and/or another attachment mechanism is configured to be connected to various other orthodontic devices, such as wires in braces or connection assemblies from other class II mechanisms, class III mechanisms, or any other class of mechanisms. In some embodiments, the cross-sectional area of the tube 773 is larger than the cross-sectional area of the slot 772. In this embodiment, the tube 773 is able to accommodate larger wires of some orthodontic devices (e.g., class II mechanisms, class III mechanisms). In this way, the connecting system provides a connection point for coupling any other orthodontic device to the patient's teeth. In some embodiments, such as the one depicted in FIG. 7A, multiple crimpable clasps 762 and associated extension arms 764 can be used on the same track 760 to provide multiple attachment mechanisms on the facial side of the patient's teeth.

In practical implementation, the bonding mechanism 770 can be bonded to the facial side of a patient's tooth using a bonding medium. The bonding medium can further be placed over other portions of the connection system, such as over the extension arm 764 and/or the extension attachment 766. Bonding medium on the occlusal side of the tooth over the extension arm 764 and/or the extension attachment 766 may prevent injury to the patient and/or damage to the extension arm 764 from the patient biting down. Bonding medium on the facial side of the tooth over the extension attachment 766 may prevent the extension attachment 766 from irritating the patient's check.

Referring back to FIGS. 2A to 2E, one way in which the appliance can function efficiently is make a proper initial placement of the sheaths 210. Each of the sheaths 210 can be placed clinically such that it is located at the gingival one third of the lingual of the anterior teeth and wires 206 make a direct path to the attachment portions 204. This placement ensures that the force created by the loaded spring 216 anchored against the molar advance the front teeth more bodily and less tipping by application of the force more toward the gingival part of the crown of the anterior teeth.

In some embodiments, the loaded spring 216 is large enough to create the desired expansion forces between the sheaths 210 and the connector tubes 208 inserted to attachment portions 204. This action causes the anterior advancement of the front teeth, transverse and horizontal expansion of the posterior teeth and distalization force on the molars to move them posteriorly.

If the distalization of the molars is indicated, with proper anchorage preparation of the front teeth and bicuspids by braces, the loaded spring 216 tied to the second bicuspids and force acting on the bands 222 on the first or second molars will drive the first and second molars distally if desired. When the proper movement of the molars is complete, the spring 216 can be made passive to ensure that no mesial movement of molars takes place. The wire connecting the second bicuspids is then detached. This allows the second and first bicuspids to naturally move towards the molars under the force of connective tissues.

If the constriction of the dental arches due to over-expanded upper or lower dental arch is indicated, with proper anchorage preparation of the molar and bicuspids teeth by braces, the wires 206 tied to the molar or bicuspids and force acting on the bands 222 on the first or second molars will drive the first or second molars or bicuspids lingually if desired. This can be done by use of constricting spring or rubber bands, attached to the bent anterior ends 214 of wires 206 inside the sheaths 210. The spring 216 can be shortened periodically to allow this movement. When the proper constriction of the molars is complete, the spring 216 can be made passive to ensure that no further constriction or expansion of the back teeth horizontally takes place.

To create a lateral force on the teeth, an expansion force is built into each half of the appliance. When activated, the force applied to the posterior teeth laterally by contact of the wire 206 to the back teeth, expands the posterior teeth laterally, thus putting pressure on the teeth. The force created by this action aids in the correction of constriction of the dental arch to resolve the crowding of the teeth. It also provides proper space for anterior positioning of the tongue forward and away from pharyngeal airway. Any outward lateral movement of the teeth creates more room for the teeth and tongue. The force created by this action in the upper jaw by expanding the upper jaw bones building the floor and lateral walls of the nasal cavity aids in the correction of constriction of nasal cavity by spreading the upper jaw bones outwardly to resolve the resistance to the air passage.

When all tooth movement is complete, the appliance 200 is inactivated automatically and now used as a retention device to hold the lateral and frontal expansion of the dental arches. At the completion of this stage, the appliance 200 can be disconnected by cutting the wires 206 and disengaging the connections of the inserts 220 and the slots 224. The bands 222 can be left in place and used for the continuation of orthodontic treatment. As described previously, in some embodiments, the bands 222 have connecting pieces 234 attached to their buccal side which allows for the attachment of various other types of orthodontic devices.

The appliance 200 also includes structure permitting selective limitation of the degree of arch spread. Referring still to FIG. 2, the anterior end 214 of each wire 206 that is received within the sheath 210 is bent in the shape of a hook. By tying these anterior ends 214 (e.g., using stainless steel wire), the lateral expansion of the appliance 200 can be stopped short of final expansion limit. In case the full expansion capability of appliance is desired, then this process continues until the anterior end 214 of the wire 206 is touching the lateral side of the opening 212 inside sheath 210 preventing further withdrawal of the wire 206 from the sheath 210, and thereby limiting spread of the patient's arch to this predetermined extent.

Figure 8:
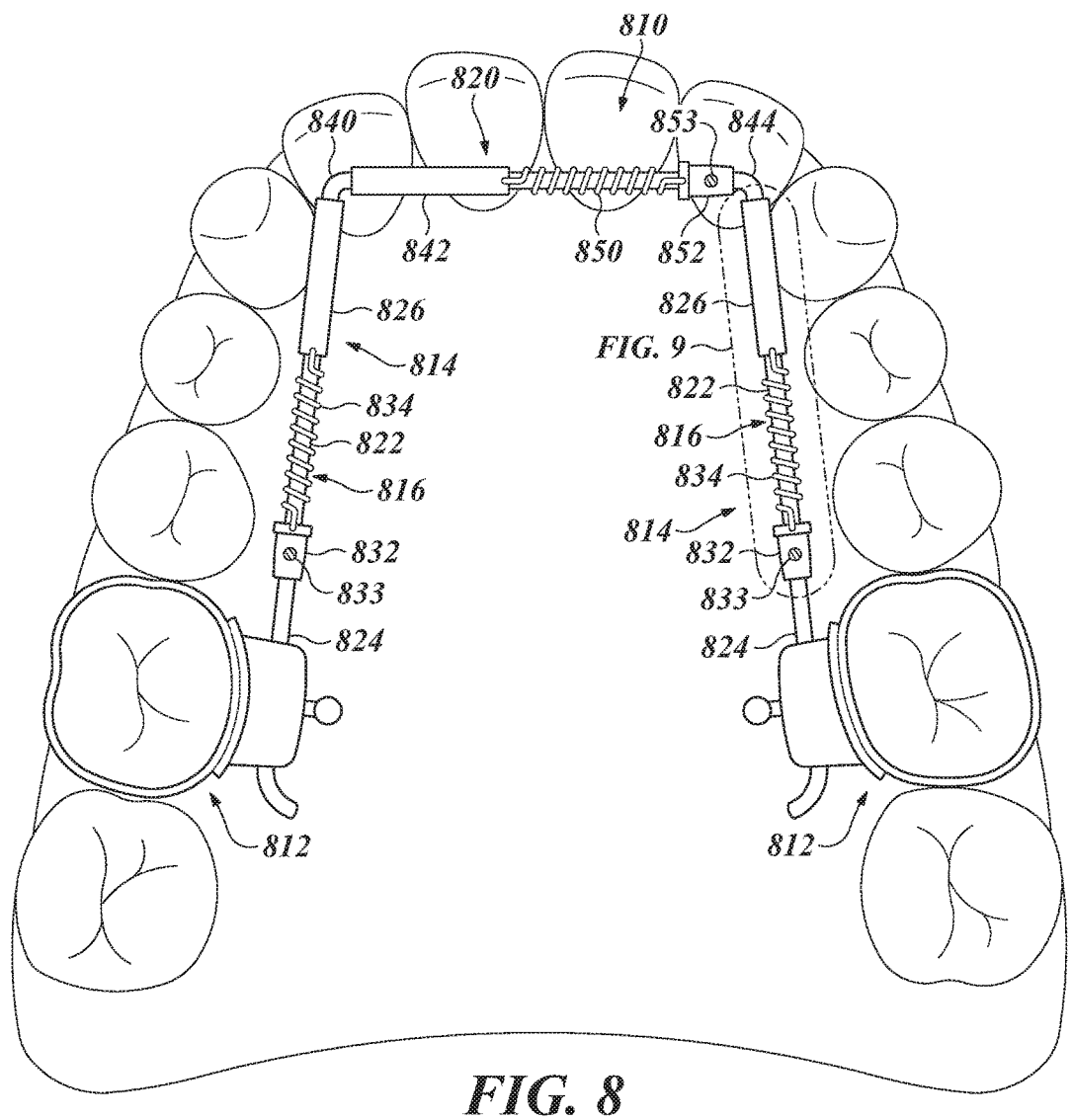
FIG. 8 is a bottom view of an alternative embodiment of dental arch and airway expander orthodontic appliance, being worn on the upper jaw and teeth of a patient.
Figure 9:
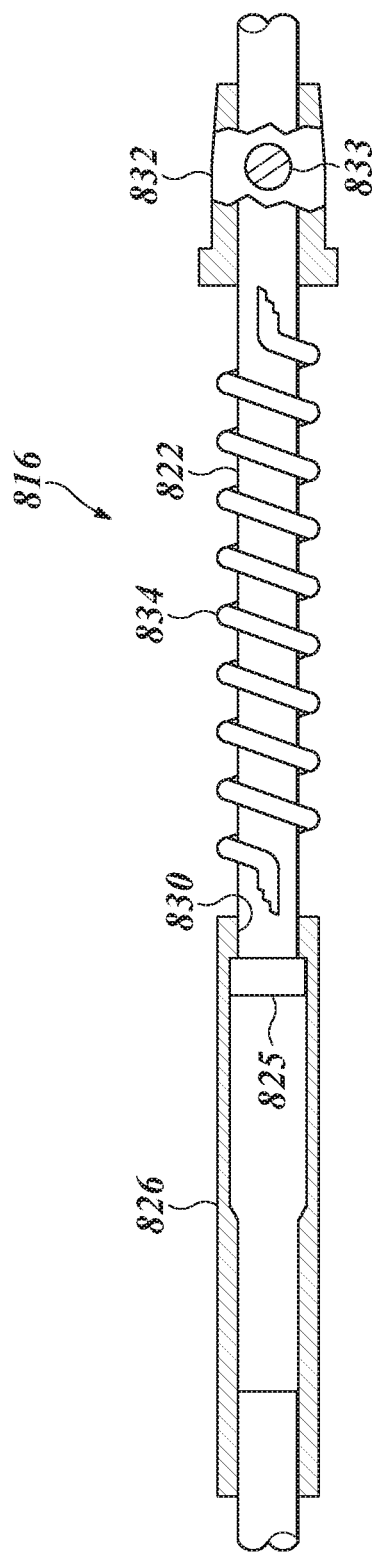
FIG. 9 is an expanded detail view of a portion of the expander of FIG. 8.

Referring, now, to FIGS. 8 and 9, a further preferred embodiment of an airway expander 810 includes tooth attachment units 812 and an expandable frame 814. Attachment units 812 are the same as attachment portions 204, and in one preferred embodiment include a connecting piece similar to connecting piece 234, as shown in FIG. 2A and described in accompanying text. Expandable frame 814 includes first and second selectively expandable arms 816, each joined to one of the attachment units 812 and being joined together by a selectively expandable anterior bridge 820. Each arm 816 includes an arm shaft 822 having a first end 824 attached to one of the attachment units 812 and a second end having a head 825 (FIG. 9), that is expanded in transverse dimension. For each arm 816, an arm sheath 826, receives the head 825, which is captured by a narrowed sheath exit 830 (FIG. 9). Further, a position-adjustable block 832, is positioned on each shaft 822 and is locked in place by a set screw 833. A spring 834 is positioned about the shaft 822. Each spring 834 has a first end joined to the sheath 826 and a second end joined to the block 832.

The bridge 820 includes a first bridge shaft 840 attached to a first one of the arm sheaths 826. Shaft 840 bends inwardly toward the center of the patient's mouth and supports a bridge sheath 842. A second bridge shaft 844 is attached to a second one of the arm sheaths 826 and also bends toward the center of the patient's mouth. The second bridge shaft 844 terminates in a head 846 (not shown, but same as head 825) that is retained in sheath 842. A spring 850 and a position-adjustable block 852, held in place by a set screw 853, are situated on the second bridge shaft 844. Blocks 832 and 852 may assume forms different from those shown. In one embodiment shafts 822 and 844 have helical threads and the positional-adjustable blocks rotated to move in position.

The advantages of the above described arrangement include the ability to push the molars backward, pull them forward, push them outwardly or even pull them inwardly. To push the molars backward, blocks 832 are moved forward, placing springs 834 into compression, and locked in place by set screws 833. The rearward force applied to the molars is a function of the compression of springs 834 and may be set to achieve a desired result. If this action causes heads 825 to abut narrowed regions 830, the effective length of shafts 822 may be increased by moving tooth attachment units rearwardly on shafts 822. To pull the molars forward, blocks 834 are moved rearward to place springs 834 into tension. Similarly, to spread the molars, bridge block 852 is moved toward bridge sheath 842. To pull molars inwardly (not a typical goal of orthodontics) block 852 is moved away from sheath 842. Although the above discussion has been directed to molars, attachment units 812 could be attached to other types of teeth and similar procedures could be performed on, for example, the bicuspids.

The methods and appliances described herein include automatic inactivation for the transverse expansion or constriction of posterior teeth, anterior advancement or retraction of the anterior teeth and distal expansion of the molars, bicuspids and canines. These methods and appliances are capable of being used for correction of the upper dental arch, upper jaw bone constriction, or lower dental arch constriction which helps to resolve the dental malposition, dental crowding, proper room for tongue position, and nasal cavity expansion for improvement of airway. In some embodiments, the appliances include loaded springs around wires connected to attachment portions with connector tubes and extended to an anterior sheath. The spring creates a distalization force on the first and/or second molars, an anterior extending force on anterior teeth (e.g., canines and incisors), and transverse expansion for the posterior teeth (e.g., canines, bicuspids, and molars).

While illustrative embodiments have been illustrated and described, it will be appreciated that various changes can be made therein without departing from the spirit and scope of the invention.

The embodiments of the invention in which an exclusive property or privilege is claimed are defined as follows:

1. An orthodontic appliance for treatment of a patient, comprising:

a. left and right attachment units, structured to be secured respectively to left and right molars, joined together by an expandable frame;
b. wherein said expandable frame includes first and second selectively expandable arms, each joined to one of said left and right attachment units and being joined together by a selectively expandable anterior bridge, said selectively expandable anterior bridge, when expanded, pushes said first and second selectively expandable arms further apart;
c. wherein each said first and second selectively expandable arms includes:
   i. an arm shaft having a first end attached to one of said left and right attachment units and a second end having a head expanded in transverse dimension;
   ii. an arm sheath, receiving said head expanded in transverse dimension, which is captured by a narrowed sheath exit;
   iii. an arm position-adjustable block, positioned on said arm shaft, outside of said arm sheath, and including a position lock;
   iv. an arm spring positioned around said arm shaft and having a first end joined to said arm sheath and a second end joined to said arm position-adjustable block;
d. wherein said selectively expandable anterior bridge includes:
   i. a first bridge shaft attached to said arm sheath of said first selectively expandable arm, said first bridge shaft having a bend and supporting a bridge sheath;
   ii. a second bridge shaft attached to said arm sheath of said second selectively expandable arm, and bending inwardly toward said bridge sheath, and having an expanded in transverse dimension head, retained in said bridge sheath by a narrowed exit;
   iii. a bridge position-adjustable block, positioned on said second bridge shaft, outside of said bridge sheath, and including a position lock;
   iv. a bridge spring positioned around said second bridge shaft and having a first end joined to said bridge sheath and a second end joined to said bridge position-adjustable block;
e. whereby a user-selectable force, chosen from a set of two alternative force applications that consists of:
   i. a force application of pushing rearward; and
   ii. a force application of pulling forward may be applied to either molar by changing the position of either arm position-adjustable block, to place either arm spring into a state selected from a set of two alternative states that consist of:
   i. a state of compression and;
   ii. a state of tension; and
f. whereby a user-selectable force, chosen from a set of two alternative force applications that consists of:
   i. a force application of pushing outward; and
   ii. a force application of pulling inward may be applied to both molars by changing the position of said bridge position-adjustable block, to place said bridge spring into a state selected from a set of two alternative states that consist of:
   i. a state of compression; and
   ii. a state of tension.

2. The orthodontic appliance of claim 1, wherein said arm springs and said bridge spring are coil springs.

3. The orthodontic appliance of claim 1, wherein said position-adjustable blocks include set screws to lock said blocks in place.

4. The orthodontic appliance of claim 1, wherein said left and right attachment units are position-adjustable on said first and second position-adjustable arms and can be locked in place on said arms.

5. A method for applying a user adjustable force to the molars of a patient, comprising:
a. providing an orthodontic appliance for treatment of a patient, including:
   i. left and right attachment units, secured respectively to left and right molars, joined together by an expandable frame;
b. wherein said expandable frame includes first and second selectively expandable arms, each joined to one of said left and right attachment units and being joined together by a selectively expandable anterior bridge;
c. wherein each said first and second selectively expandable arms includes:
   i. an arm shaft having a first end attached to one of said left and right attachment units and a second end having a head expanded in transverse dimension;
   ii. an arm sheath, receiving said head expanded in transverse dimension, which is captured by a narrowed sheath exit;
   iii. an arm position-adjustable block, positioned on said arm shaft, outside of said arm sheath;
   iv. an arm spring positioned around said arm shaft and having a first end joined to said arm sheath and a second end joined to said arm position-adjustable block;
d. wherein said selectively expandable anterior bridge includes:
   i. a bridge first shaft attached to said arm sheath of said first selectively expandable arm, said first bridge shaft having a bend and supporting a bridge sheath;
   ii. a bridge second shaft attached to said arm sheath of said second selectively expandable arm, and bending inwardly toward said bridge sheath, and having an expanded in transverse dimension head, retained in said bridge sheath by a narrowed exit;
   iii. a bridge position-adjustable block, positioned on said second shaft, outside of said bridge sheath;
   iv. a bridge spring positioned around said bridge shaft and having a first end joined to said bridge sheath and a second end joined to said bridge position-adjustable block;
e. adjusting said positions of said arm position-adjustable blocks, thereby placing each said arm spring into a state, selected from a set of two alternative states that consists of:
   i. a state of compression; and
   ii. a state of tension;
   by a user selectable amount and thereby acting on each said attached molar by one out of a set of two alternative force applications, that consists of:
   i. pushing said attached molar backward; and
   ii. pulling said attached molar forward
f. adjusting said position of said bridge position-adjustable block, thereby placing said bridge spring into a state, selected from a set of two alternative states that consist of:
   i. a state of compression; and
   ii. a state of tension;
   by a user selectable amount and thereby acting on said attached molars by one out of a set of two alternative force applications, that consists of:
   i. pushing said attached molars outward; and
   ii. pulling said attached molars inward.

6. The method of claim 5, wherein said left and right attachment units are position-adjustable on said arms and can be locked in place on said arms and can be moved on said arms and locked in place in a new position.

\* \* \* \* \*